US008182468B2

(12) United States Patent
Yokota et al.

(10) Patent No.: US 8,182,468 B2
(45) Date of Patent: May 22, 2012

(54) CONNECTOR AND INFUSION TUBE SET

(75) Inventors: Takayuki Yokota, Nakakoma-gun (JP); Yoshinori Hishikawa, Nakakoma-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 132 days.

(21) Appl. No.: 12/446,918

(22) PCT Filed: Nov. 5, 2007

(86) PCT No.: PCT/JP2007/071492
§ 371 (c)(1),
(2), (4) Date: Apr. 23, 2009

(87) PCT Pub. No.: WO2008/056631
PCT Pub. Date: May 15, 2008

(65) Prior Publication Data
US 2010/0030194 A1   Feb. 4, 2010

(30) Foreign Application Priority Data

Nov. 6, 2006  (JP) .................................. 2006-300732

(51) Int. Cl.
*A61M 25/16* (2006.01)
(52) U.S. Cl. ..................................................... 604/535
(58) Field of Classification Search .................. 604/284, 604/533, 535, 534, 523; 403/169, 345
See application file for complete search history.

(56) References Cited

U.S. PATENT DOCUMENTS 4,588,402 A * 5/1986 Igari et al. ..................... 604/408
4,826,477 A * 5/1989 Adams  604/4.01
6,077,259 A   6/2000 Caizza et al.
2008/0103484 A1   5/2008 Hishikawa et al.

FOREIGN PATENT DOCUMENTS

| JP | 2000-107300 A | 4/2000 |
|---|---|---|
| JP | 2004-49319 A | 2/2004 |
| WO | WO 2006/068211 A1 | 6/2006 |

OTHER PUBLICATIONS

International Search Report (PCT/ISA/210) Jan. 28, 2008.
Written Opinion (PCT/ISA/237) Jan. 28, 2008.

* cited by examiner

*Primary Examiner* — (Jackie) Tan-Uyen T. Ho
*Assistant Examiner* — Imani Hayman
(74) *Attorney, Agent, or Firm* — Buchanan Ingersoll & Rooney PC

(57) ABSTRACT

A connector includes a male connector section having a male-side cavity, a female connector section having a female-side cavity to which another male connector section the same as the male connector section can be connected, a seal member formed from an elastic material for maintaining liquid tightness between the connector sections when the other male connector section and the female connector section are connected to each other, and lock mechanisms disposed respectively on the male connector section side and the female connector section side for maintaining the connected condition of the connector sections when the other male connector section and the female connector section are connected to each other. Each of the lock mechanisms has a male lock section formed to project in parallel to the direction of connection between the connector sections, and a female lock section, which is formed adjacent to the male lock section and parallel to the direction of connection, and to which another male lock section the same as the male lock section can be coupled.

16 Claims, 11 Drawing Sheets

CONNECTOR AND INFUSION TUBE SET

TECHNICAL FIELD

The present invention relates to a connector and an infusion tube set having the same.

BACKGROUND ART

In medical appliances requiring connection of passages for liquid(s) to be used for infusion, transfusion, nutrient dosing or the like, the liquid passages (circuits) must be connected and disconnected as required, when sustainedly or momentarily causing a flow of the liquid(s), such as a liquid medicine, blood, and liquid food. In such a situation, it is known to attach a connection means for connecting the liquid passages to an intermediate portion of the circuit. Typical examples of the connection means include the one described in Patent Document 1.

The connection means (connector) includes a male connector section, a male lock section provided adjacent (correspondingly) to the male connector section, a female connector section, and a female lock section provided adjacent to the female connector section. When connection means having such a configuration are connected to each other, the male lock section on one side and the female lock section on the other side engage with each other in a locked condition, and the male connector section on one side and the female connector section on the other side communicate with each other to permit liquid to flow therethrough. At the time of releasing the locked condition of the connectors thus connected to each other, an operating piece (operating part) provided on the female lock section is pressed, whereby engagement between the lock sections is released, and hence the locked condition can be released.

Thus, in the connector according to the related art (described in Patent Document 1), one connector section is provided with one lock section, as mentioned above. Therefore, there is a concern that when, for example, the connector in the connected condition is grasped, the operating piece on the female lock section might be pressed by mistake, unintentionally resulting in release of the locked condition.

Patent Document 1: International Publication No. WO 2006/068211

DISCLOSURE OF INVENTION

It is an object of the present invention to provide a connector and an infusion tube set, in which unintended release of a connected condition can securely be prevented from occurring.

In order to attain the above object, the present invention provides a connector including:

a male connector section having a male-side cavity;

a female connector section having a female-side cavity to which another male connector section the same as the male connector section can be connected;

a seal member formed from an elastic material for maintaining liquid tightness between the connector sections when the other male connector section and the female connector section are connected to each other; and lock mechanisms disposed respectively on the male connector section side and the female connector section side for maintaining a connected condition of the connector sections when the other male connector section and the female connector section are connected to each other;

wherein each of the lock mechanisms has a male lock section formed to project in parallel to the direction of connection between the connector sections, and a female lock section, which is formed adjacent to the male lock section and parallel to the direction of connection, and to which another male lock section the same as the male lock section can be coupled.

This makes it possible to securely prevent the connected condition from being released unintentionally.

In addition, in the connector according to the present invention, preferably, in the connected condition, the male-side cavity of the other male connector section and the female-side cavity of the female connector section communicate with each other so as to permit a liquid to flow therethrough.

This ensures that at the time of performing an infusion, transfusion, nutrient dosing or the like, for example, the liquid (e.g., infusion, blood, or nutrient agent) can pass smoothly.

Further, in the connector according to the present invention, preferably, each of the male connector section and the female connector section is tubular in shape, and the male lock section and the female lock section are disposed symmetrically about a center axis of the connector section.

This ensures that at the time of connection between the female connector section and the other male connector section, the connector sections are easily connected to each other rectilinearly.

Further, in the connector according to the present invention, preferably, the male lock section has a pair of long claw parts capable of moving toward and away from each other, and an urging part provided on one end side of both of the claw parts and operative to urge the claw parts, so as to move the claw parts away from each other on the other end side. Also, the female lock section has engaging parts capable of engagement respectively with the claw parts of the other male lock section, which are the same as the claw parts of the male lock section, and an operating part operable to cause both the claw parts of the other male lock section, which are the same as the claw parts of the male lock section, to move toward each other.

This ensures that the female lock section and the other male lock section are securely placed in the locked condition. Further, the locked condition can be assuredly released by operating the operating part.

In addition, in the connector according to the present invention, preferably, each of the male connector section and the female connector section is tubular in shape, and pluralities of the male lock sections and the female lock sections are arranged along an outer circumferential direction of the connector section.

This ensures that when the female lock sections and the other male lock sections are connected to each other, the condition (connected condition) is maintained more rigidly, so that unintentional release of the connected condition can be prevented more reliably.

Further, in the connector according to the present invention, preferably, the male lock sections and the female lock sections are alternately arranged.

This ensures that when the female lock sections and the other male lock sections are connected to each other, the condition (connected condition) is maintained more rigidly, so that unintentional release of the connected condition can be prevented more reliably.

Further, in the connector according to the present invention, preferably, each of the male connector section and the female connector section is tubular in shape;

the lock mechanisms are disposed respectively on an outer peripheral part of the connector section, and are substantially cylindrical in overall shape; and the cylindrical wall part is provided with a plurality of deficit portions, where material is made deficient in long-shaped areas along the center axis direction, the female lock sections being constituted by the deficit portions, and the male lock sections being constituted by parts of the wall part that are located between adjacent ones of the deficit portions.

This ensures that when the female lock sections and the other male lock sections are connected to each other, the condition (connected condition) is maintained more rigidly, so that unintentional release of the connected condition can be prevented more reliably.

In addition, in the connector according to the present invention, preferably, each of the lock mechanisms can be used at any of a plurality of rotational angles about the center axis of the connector section.

This ensures that in a case where, for example, a tube is connected to the connector, even if the tube is twisted, twisting of the tube can be eliminated by rotating the connector in reverse to the direction of twisting.

Further, in the connector according to the present invention, preferably, the seal member is fixed to the female-side cavity of the female connector section, and has a surface, which is placed in secure contact with an end part of the other male connector section in the locked condition, and a slit formed in the surface, which is opened in the locked condition.

This ensures that, in the connected condition, the female connector section and the other male connector section are securely connected in a liquid-tight manner, and can communicate with each other assuredly.

Further, the connector according to the present invention, preferably, includes a plurality of female connector sections, wherein at least one of the female connector sections and the male connector section are disposed such that center lines thereof are substantially orthogonal to each other.

This ensures that the direction(s) of flow of a liquid or liquids passing through the connector can be changed.

In addition, the connector according to the present invention, preferably, includes a plurality of female connector sections, wherein at least one of the female connector sections and the male connector section are disposed so that center lines thereof are parallel to each other, and an opening part of the female connector section and an opening part of the male connector section are oriented in opposite directions.

This ensures that when two connectors are connected to each other, for example, the connectors can be connected to each other substantially rectilinearly by connecting the male connector section on one (or the other) side and the other female connector section to each other.

In order to attain the above object, the present invention also provides an infusion tube set including:

the connector according to the present invention; and a tube assembly having a tube, and a tube-side connector, which is disposed at one end part of the tube, and which can be connected to the connector.

This ensures that unintentional release of the connected condition can be prevented reliably.

BEST MODE FOR CARRYING OUT THE INVENTION

The connector and the infusion tube set according to the present invention will be described in detail below, based on preferred embodiments thereof shown in the accompanying drawings.

First Embodiment

Figure 1:
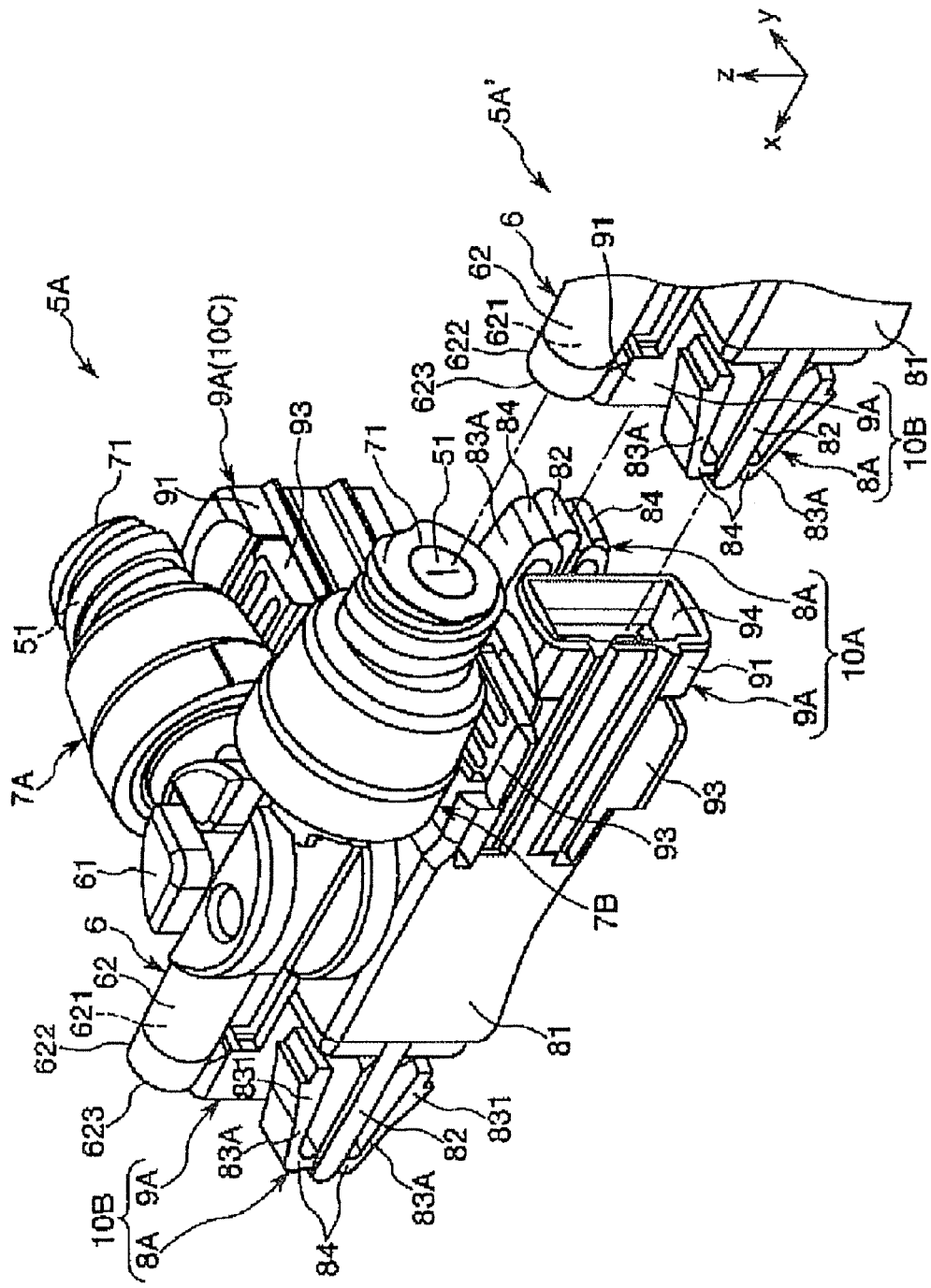
FIG. 1 is a perspective view showing a first embodiment of the connector according to the present invention.
Figure 2:
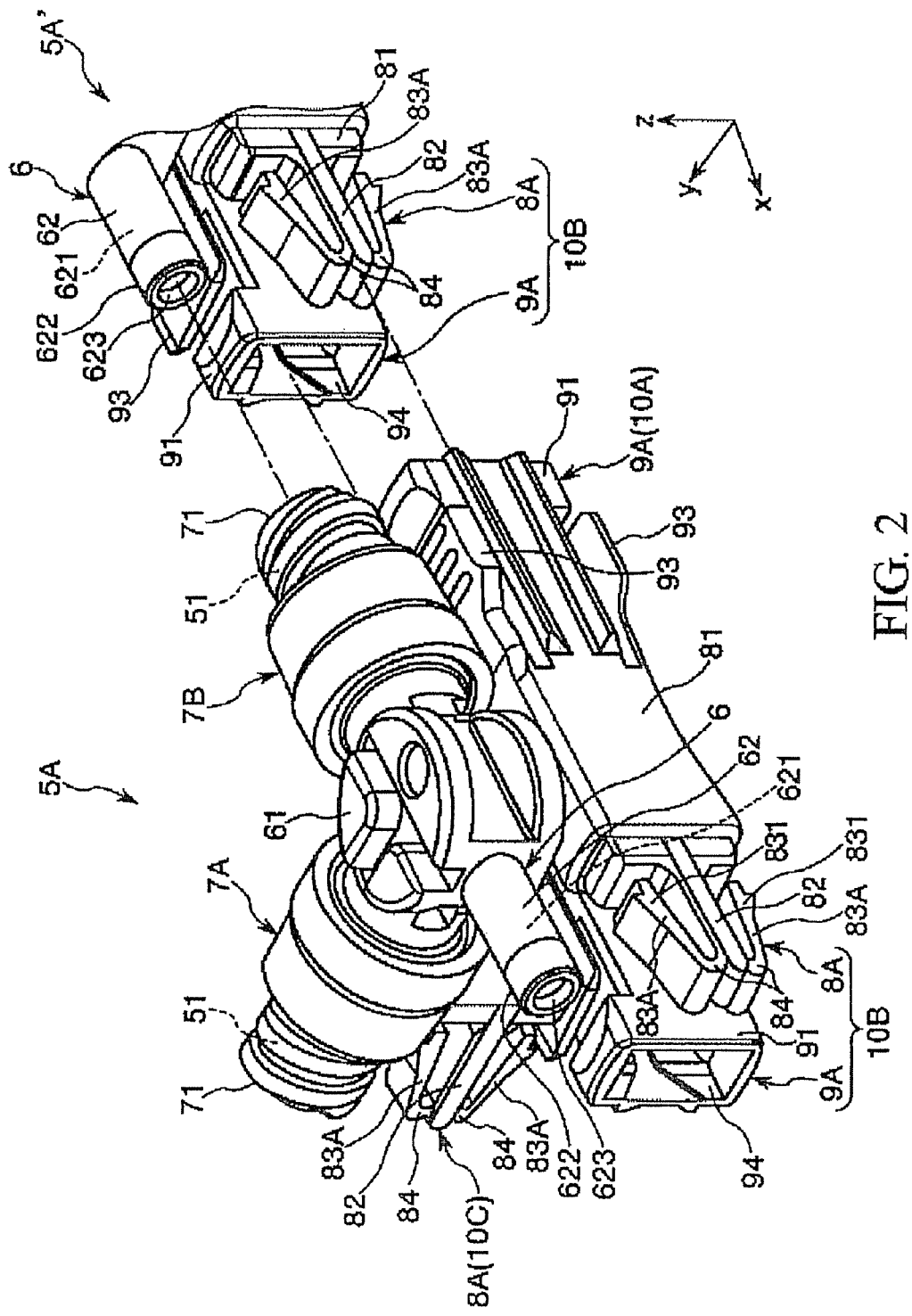
FIG. 2 is a perspective view showing the first embodiment of the present invention.
Figure 3:
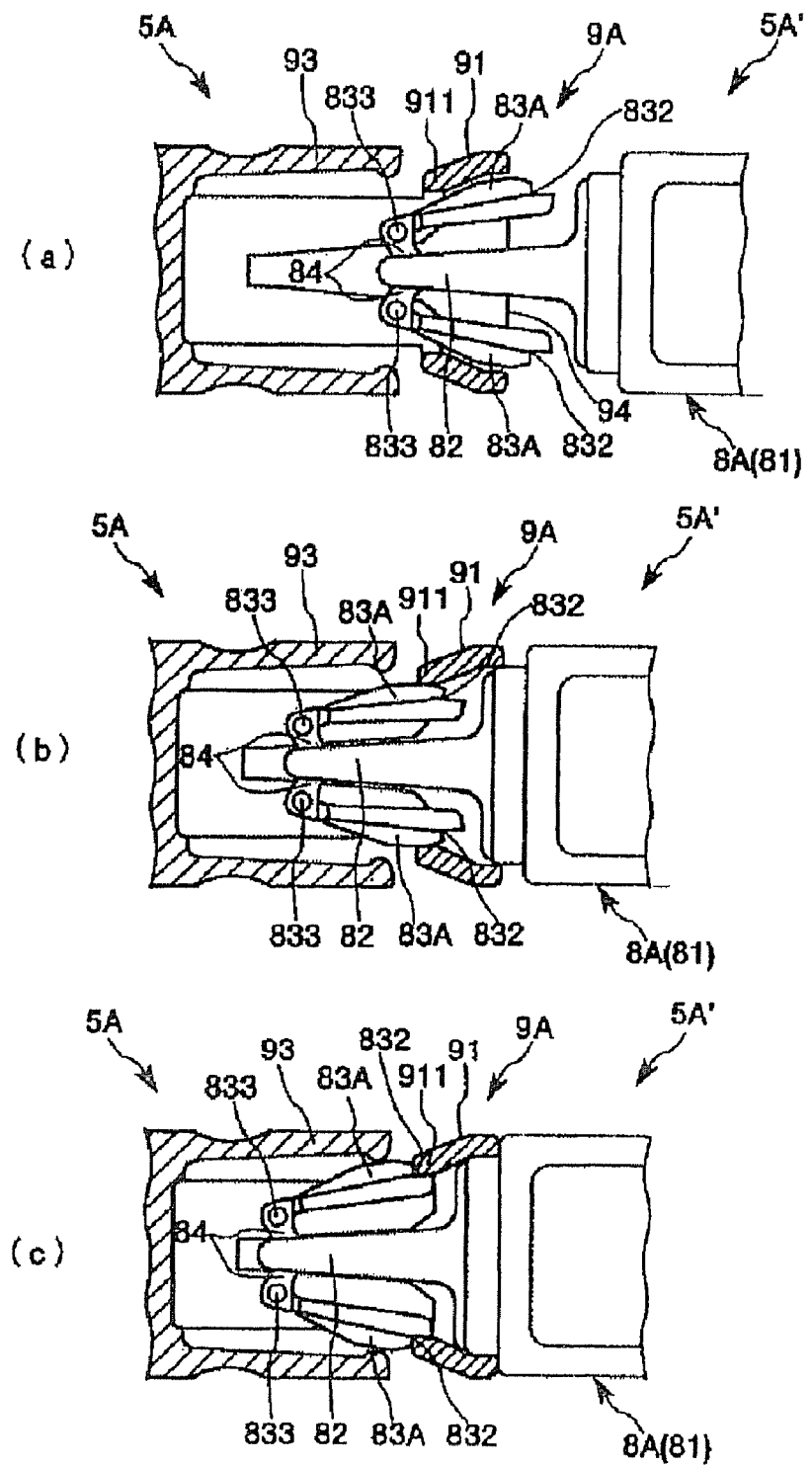
FIG. 3 shows views (partial longitudinal sectional views) sequentially illustrating a connected condition of the connector shown in FIG. 1 (also in FIG. 2)
Figure 4:
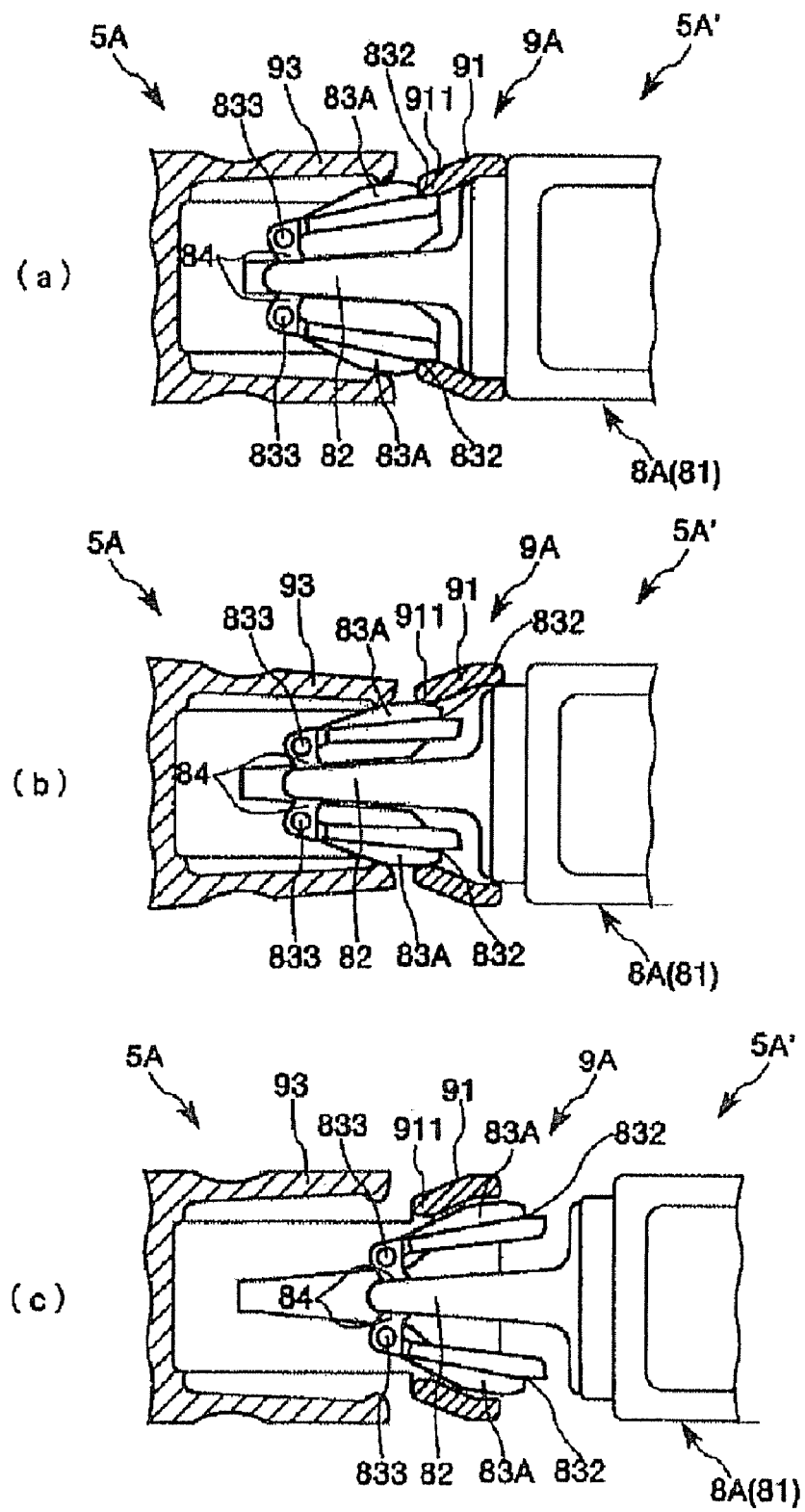
FIG. 4 shows views (partial longitudinal sectional views) sequentially illustrating a disconnected condition of the connector shown in FIG. 1.
Figure 5:
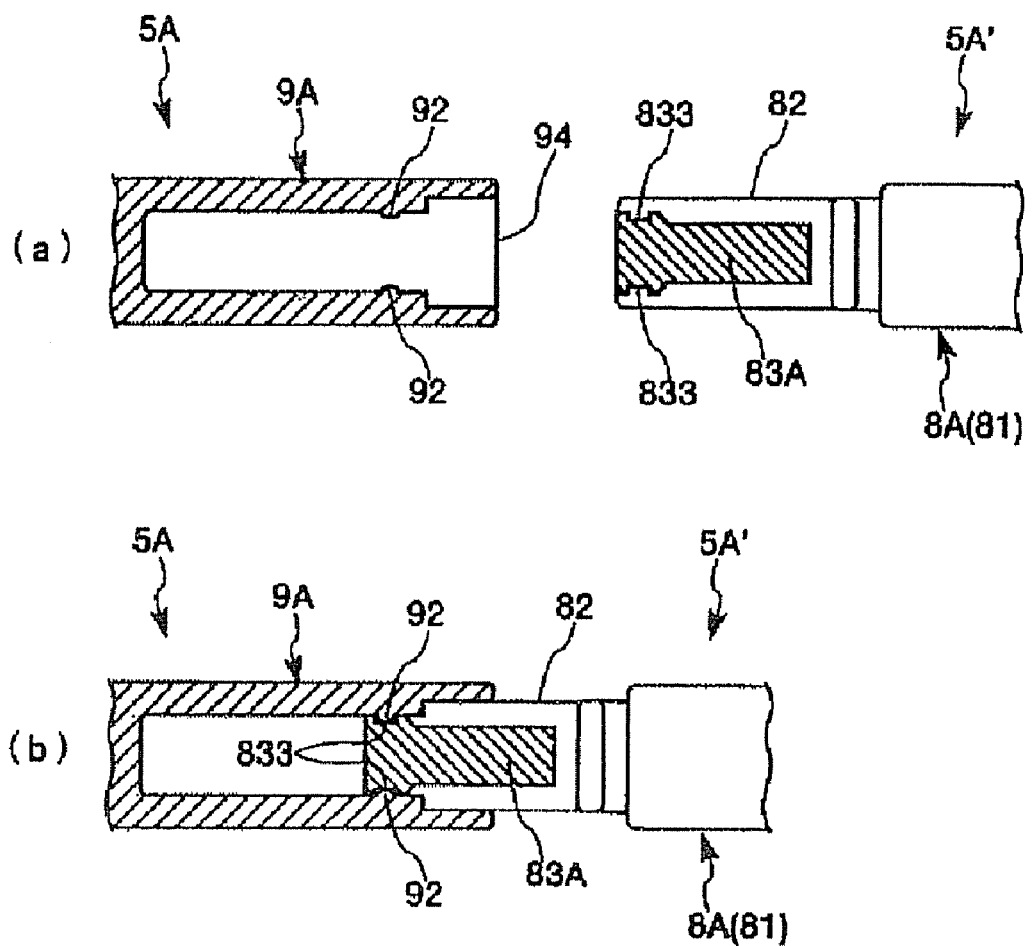
FIG. 5 shows views (longitudinal sectional views) sequentially illustrating a connected condition of the connector shown in FIG. 1.
Figure 6:
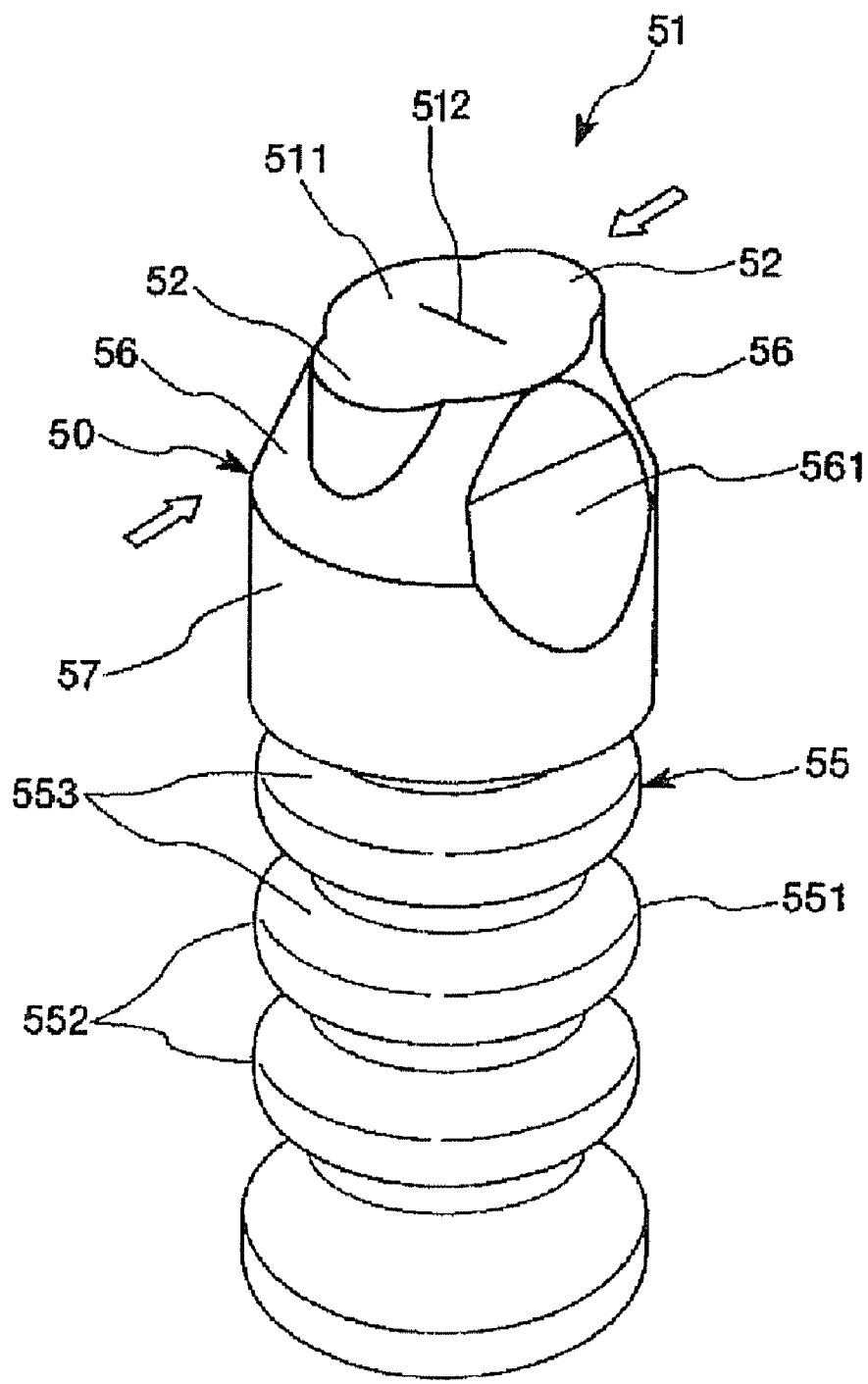
FIG. 6 is a perspective view showing a valve element (seal member) possessed by the connector shown in FIG. 1.
Figure 7:
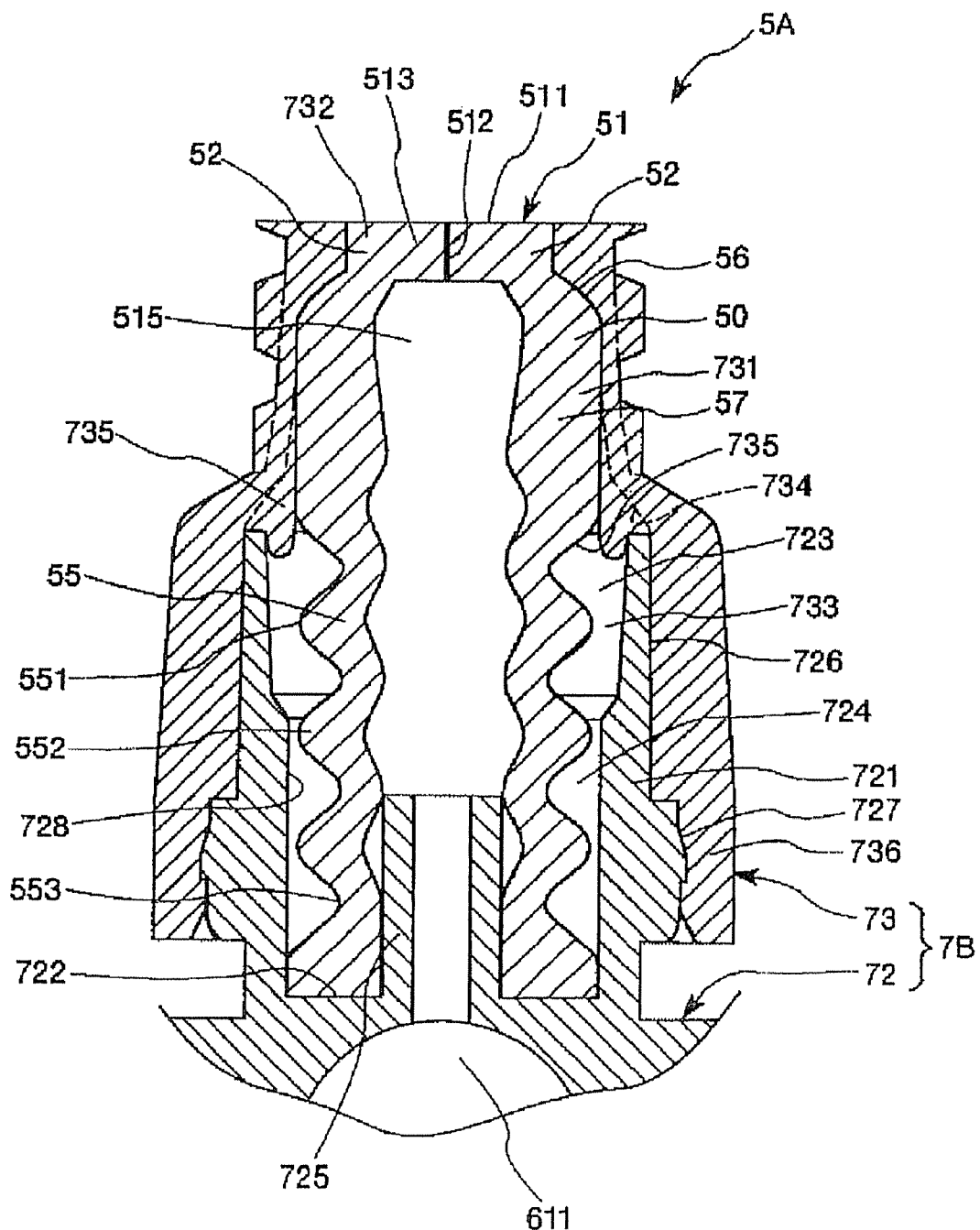
FIG. 7 is a view sequentially illustrating a connected condition of the connector shown in FIG. 1.
Figure 8:
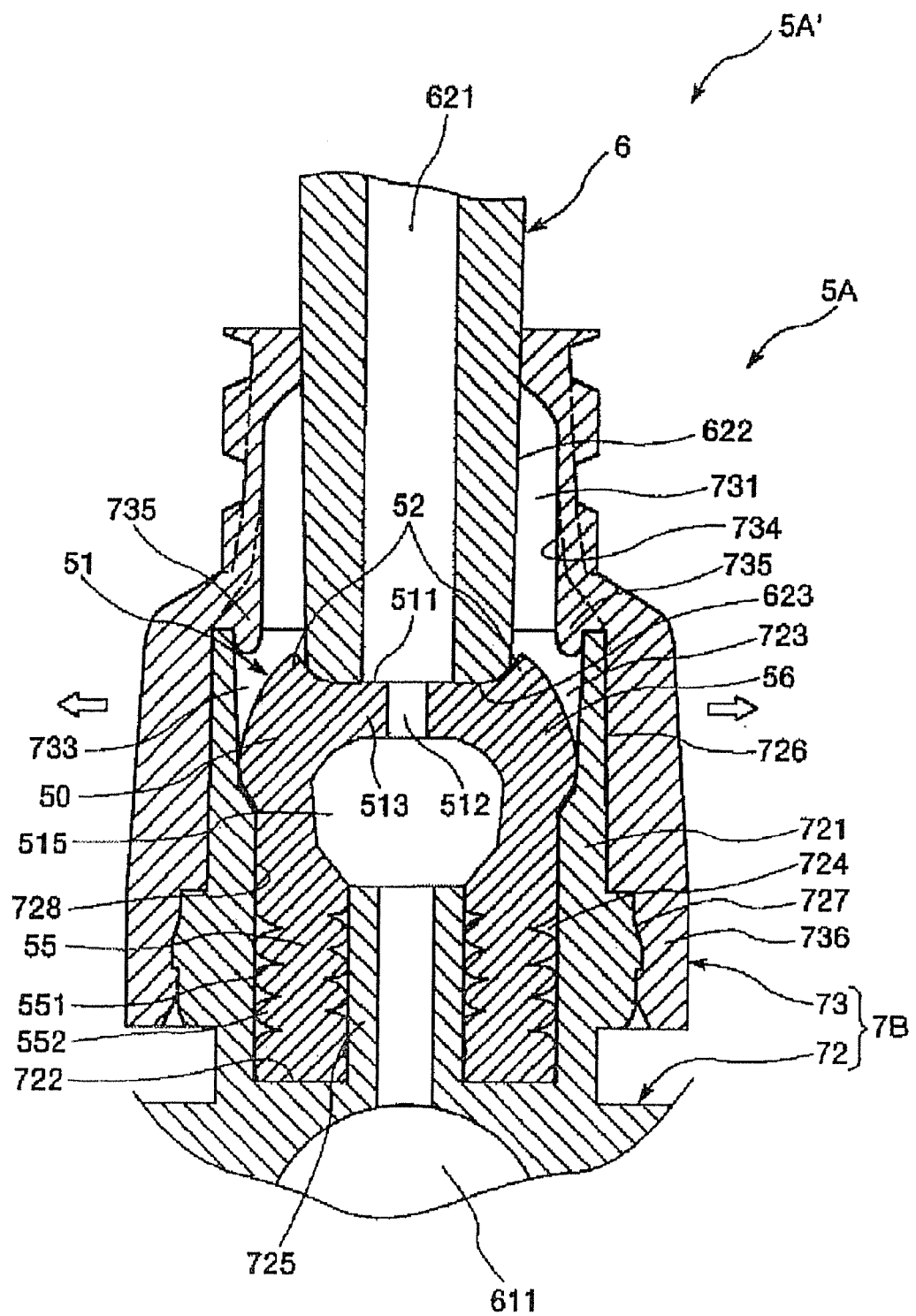
FIG. 8 is a view sequentially illustrating a connected condition of the connector shown in FIG. 1.
Figure 9:
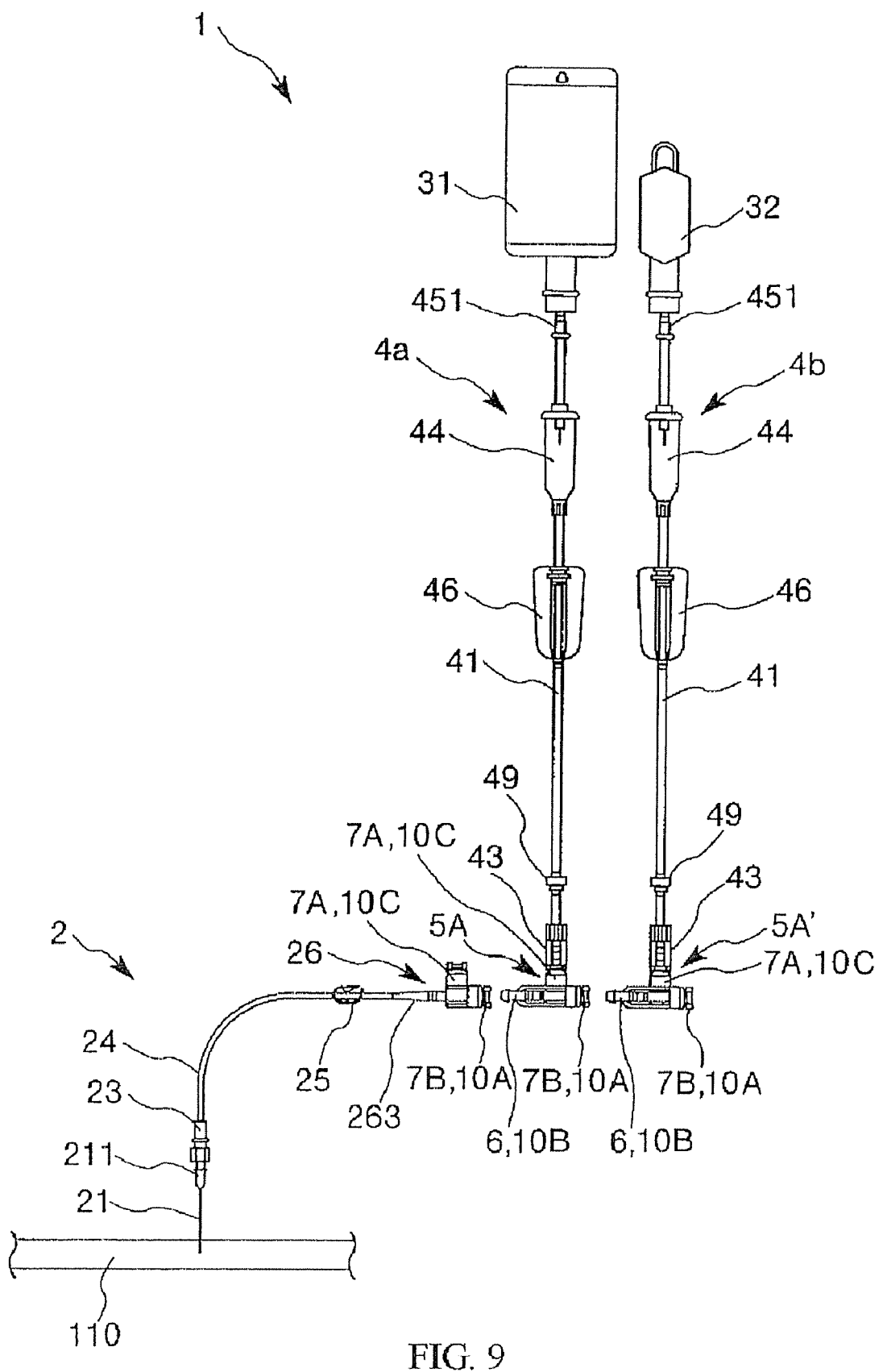
FIG. 9 is a plan view of an infusion tube set according to the present invention, which includes the connector shown in FIG. 1.
Figure 10:
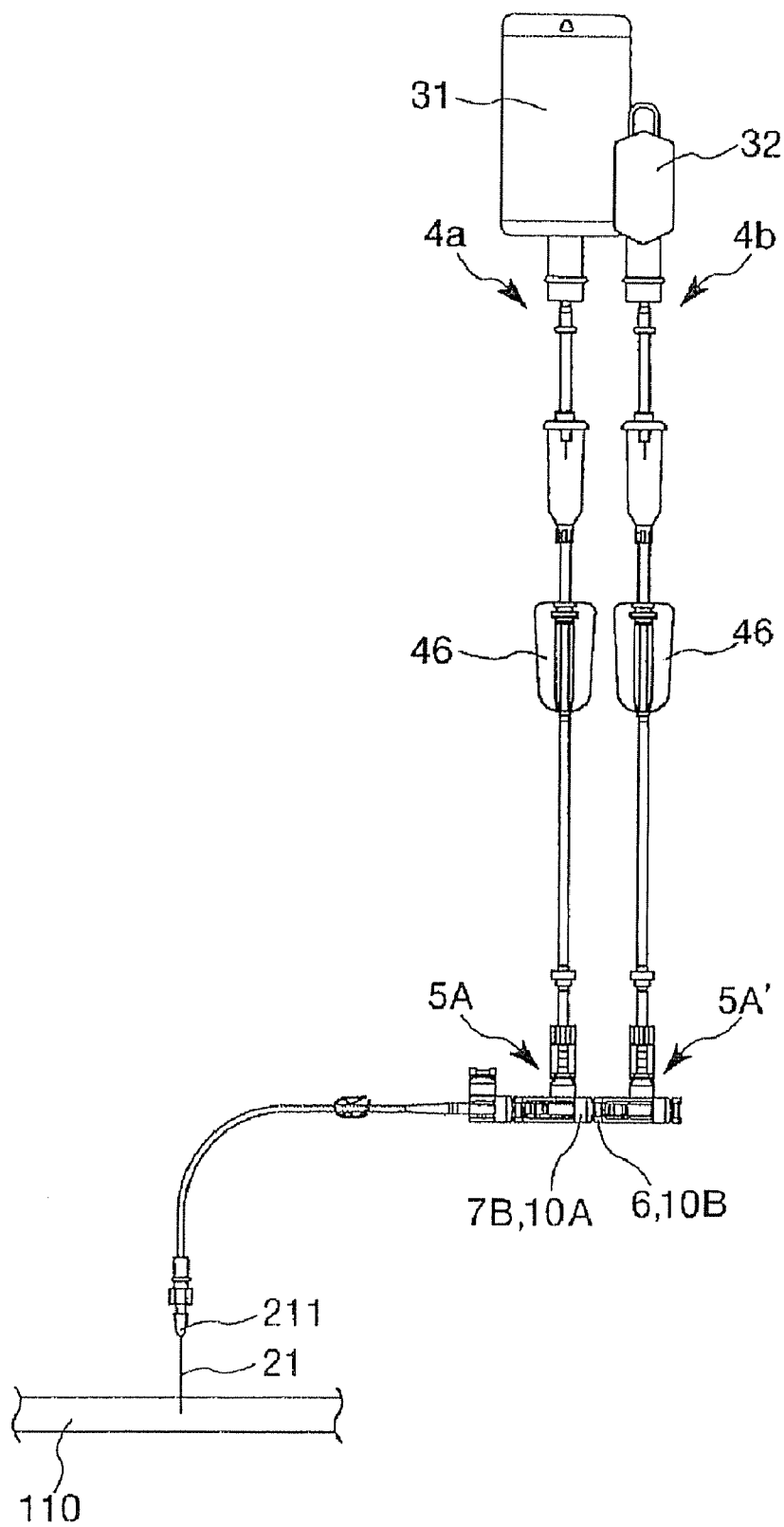
FIG. 10 is a plan view showing the infusion tube set shown in FIG. 9, in a condition where each infusion tube has been connected.

FIGS. 1 and 2 are perspective views showing a first embodiment of the connector according to the present invention; FIG. 3 shows views (partial longitudinal sectional views) sequentially illustrating a connected condition of the connector shown in FIG. 1 (also in FIG. 2); FIG. 4 shows views (partial longitudinal sectional views) sequentially illustrating a disconnected condition of the connector shown in FIG. 1; FIG. 5 shows views (longitudinal sectional views) sequentially illustrating a connected condition of the connector shown in FIG. 1; FIG. 6 is a perspective view showing a valve element (seal member) possessed by the connector shown in FIG. 1; FIGS. 7 and 8 are views sequentially illustrating a connected condition of the connector shown in FIG. 1; FIG. 9 is a plan view of an infusion tube set according to the present invention, which includes the connector shown in FIG. 1; and FIG. 10 is a plan view showing the infusion tube set shown in FIG. 9, in a condition where each infusion tube has been connected. Incidentally, for facilitating descriptions thereof, the longitudinal direction of the connector will be referred to as an "x-axis direction," and directions perpendicular to the x-axis direction will be referred to as a "y-axis direction" and "z-axis direction" respectively. Further, in the following descriptions, in FIGS. 6 to 10, the lower side will be referred to as a "distal" side and the upper side as a "proximal" side.

The infusion tube set (infusion set) 1 shown in FIGS. 9 and 10 is an apparatus (set) utilized for injecting (administering) an infusion into a living organism (patient).

The term infusion includes all liquids that can be administered to living organisms, for example, liquid medicines, correcting electrolytes, and physiological saline.

In addition, the drug in the liquid medicine is not particularly limited, and may be any drug, such as a sedative, intravenous anesthetic, anesthetic analgesic, local anesthetic, antidepolarizing muscle relaxant, vasopressor, depressor, coronary vasodilator, diuretic, antiarrhythmic agent, bronchodilator, styptic, vitamin agents, antibiotic agents, and a lipid emulsion.

As shown in FIG. 9, the infusion tube set 1 includes a first infusion tube (first tube assembly) 4b, a second infusion tube (second tube assembly) 4a, a connector 5A to which one end part of the second infusion tube 4a can be connected, a connector 5A' to which one end part of the first infusion tube 4b can be connected, piercing needles (hollow needles or spikes) 451 (connecting parts) provided respectively at other end parts of the first infusion tube 4b and the second infusion tube 4a, and an infusion dosing section 2 for dosing a patient with an infusion or infusions. These components will be described sequentially below.

As shown in FIG. 1, the connector 5A on the first infusion tube 4b side (the left side in FIG. 9) includes a male connector section 6, female connector sections 7A and 7B, lock mechanisms 10A, 10B and 10C, and a valve element (seal member) 51. Similar to the connector 5A, the connector 5A' on the second infusion tube 4a side (the right side in FIG. 9) also includes a male connector section 6, female connector sections 7A and 7B, lock mechanisms 10A, 10B and 10C, and a valve element (seal member) 51. Thus, the connector 5A and the connector 5A' are substantially the same in configuration. Taking this into account, the connector 5A on the second infusion tube 4a side will be described below as representative.

As shown in FIG. 1, the male connector section 6 has a male connector section main body 61, and a tubular section 62.

The tubular section 62 is formed to project in the x-axis positive direction from the male connector section main body 61. The tubular section 62 has a liquid passage (male-side cavity) 621 through which liquid passes, and a luer tapered part 622.

The liquid passage 621 communicates with the interior of the male connector section main body 61.

The luer tapered part 622 is formed on an outer peripheral part of the male connector section 6, which is on the side of an opening part 623, in such a manner that the outside diameter thereof gradually decreases toward the opening part 623.

Each of the female connector sections 7A and 7B forms a portion to which the male connector section 6 of the connector 5A' can be connected, respectively. The female connector section 7A and the female connector section 7B are substantially the same in shape (configuration); taking this into consideration, the female connector section 7B will be described below as representative.

As shown in FIG. 7 (also in FIG. 8), the female connector section 7B has a female connector section main body 72, and a cap section (cap) 73.

The female connector section main body 72 shown in FIG. 7 is formed, at a distal portion thereof, with a valve element disposing section 721 having a bottomed cylindrical shape. The valve element disposing section 721 is formed with a second cavity (female-side cavity) 723 therein on the proximal side, and with a third cavity (female-side cavity) 724 on the distal side thereof, which communicates with the second cavity 723. The second cavity 723 has a larger inside diameter than a first cavity (female-side cavity) 731 formed in the cap section 73, to be described later. The third cavity 724 (an inner peripheral surface 728) has a smaller inside diameter than the second cavity 723. The inside diameter of the third cavity 724, preferably, is slightly larger than the outside diameter of a barrel part 55 (an outer peripheral surface 551) of the valve element 51, to be described later.

In addition, at a central portion of a bottom surface 722 of the female connector section main body 72, an internal projection 725 is provided, which is constituted by a tubular body. When the male connector section 6 is connected to the first cavity 731 (connection port 732) and the valve element 51 begins to be pressed, the inside portion of the valve element 51 is supported by the internal projection 725, so that buckling of the valve element 51 (bending of the valve element 51 into a V-shape) can be prevented from occurring (see FIG. 8). Further, when a liquid passes through the connector 5A, stagnation of the liquid can be prevented.

In addition, a lumen of the internal projection communicates with a passage 611, which is formed inside the male connector section main body 61, and through which liquid can pass. This ensures that the second cavity 723 and the third cavity 724 communicate with the passage 611 through the internal projection 725.

Also, on the distal side of the outer peripheral surface 726 of the valve element disposing section 721, a stepped part 727, which is set larger in diameter than the proximal side, is provided.

The cap section 73 shown in FIG. 7 is provided with a space (female-side cavity) therein containing the valve element 51. The cap section 73 is coupled to the proximal side (the valve element disposing section 721) of the female connector section main body 72.

The cap section 73 is provided with the first cavity 731 therein, in which a head part 50 of the valve element 51, to be described later, can be inserted. The cap section 73 further includes a fitting part 733, which communicates with the first cavity 731, and which is larger in diameter than the first cavity 731.

The first cavity 731 is formed in a shape corresponding to an outer shape of the head part 50 of the valve element 51. In addition, the connection port (connecting part) 732 that connects to the male connector section 6 is formed on the proximal side of the first cavity 731, and the diameter thereof is set smaller than the diameter of the first cavity 731 on the distal side.

The first cavity 731 is provided at its inner peripheral surface 734 with a plurality of ribs 735, which extend along the axial direction and project in a radial direction of the first cavity 731. When the male connector section 6 of the connector 5A' is connected to the connector 5A (the connection port 732), the valve element 51 is supported by the ribs 735, whereby buckling of the valve element 51 (and falling off of the valve element 51) can be prevented from occurring. In addition, the number of ribs 735 is not particularly limited; for example, the number is preferably two to ten, and more preferably, four to eight.

A stepped part 736, in which the stepped part 727 of the valve element disposing section 721 is to be fitted, is formed on the distal side of the fitting part 733, and the diameter thereof is set to be larger than the diameter of the fitting part 733 on the proximal side. In addition, the inside diameter of the stepped part 736, preferably, is approximately equal to or slightly smaller than the outside diameter of the stepped part 727 of the valve element disposing section 721. This enables firm fitting (coupling) (liquid-tight contact) between the cap section 73 (the stepped part 736) and the female connector section main body 72 (the stepped part 727), and thus liquid inside the connector 5A can be prevented from leaking. Further, when the cap section 73 and the female connector section main body 72 are coupled together, the first cavity 731 and the second cavity 723 communicate with each other, and the valve element 51 can be disposed (contained) within the space composed of the first cavity 731, the second cavity 723, and the third cavity 724.

Incidentally, the method for fixing the female connector section main body 72 and the cap section 73 to each other is not limited to the aforementioned fitting. For example, the method may be performed by caulking, adhesion with an adhesive, fusing such as heat fusing and ultrasonic fusing, or the like.

As shown in FIG. 1, the female connector section 7A is disposed in a y-axis positive direction in relation to the male connector section main body 61 (the male connector section 6). In other words, the female connector section 7A is disposed such that the center line thereof is substantially orthogonal to the center line of the male connector section 6.

The female connector section 7B is disposed in an x-axis negative direction in relation to the male connector section main body 61 (the male connector section 6). In other words, the female connector section 7B is disposed such that the center line thereof is parallel to the center line of the male connector section 6, and so that the opening part 71 of the female connector section 7B and an opening part 623 of the male connector section 6 are oriented in opposite directions. This ensures that when the two connectors 5A and 5A' are connected to each other, for example, the connectors 5A and 5A' can be connected substantially rectilinearly, by connecting the male connector section 6 on one side and the female connector section 7B on the other side (see FIGS. 1 and 2).

When such female connector sections 7A and 7B are provided, liquids can be fed into the male connector section 6 from two different directions, and the liquids can branch off from the male connector section 6 in two different directions.

As shown in FIGS. 7 and 8, the valve elements 51 are contained (fixed), respectively, in the female connector section 7A and the female connector section 7B.

The valve elements 51 are each formed from an elastic material. Examples of suitable elastic materials include various rubber materials such as natural rubber, isoprene rubber, butadiene rubber, styrene-butadiene rubber, nitrile rubber, chloroprene rubber, butyl rubber, acrylic rubber, ethylene-propylene rubber, hydrin rubber, urethane rubber, silicone rubber, fluororubber, etc., and various thermoplastic elastomers based on styrene, polyolefin, polyvinyl chloride, polyurethane, polyester, polyamide, polybutadiene, trans-polyisoprene, fluororubber, chlorinated polyethylene, or the like, which may be used either singly or in a mixture of two or more of them. When such an elastic material is used, an appropriate elasticity can be imparted to a top face 511 of the valve element 51, and therefore, the top face 511 can be placed in secure contact with the opening part (end part) 623 of the male connector section 6 (see FIG. 8).

As shown in FIGS. 6 and 7, the top face 511 is exposed from the opening part 71 of the female connector section 7B. Further, the top face 511 is located substantially flush with an end face of the female connector section 7A.

The head part 50 has a bottomed cylindrical shape, and is formed with a cavity 515 therein through which liquid can pass, together with a slit 512 that extends from the flat top face 511 (a bottom part 513) to reach the cavity 515. The slit 512 is formed substantially in the shape of a straight line segment.

The simple shape of the slit 512 enables easier (more assured) opening of the slit 512. In addition, the flat shape of the top face 511 permits the top face 511 (the slit 512) to be disinfected easily.

As shown in FIG. 1, the top face 511 is exposed from the opening part 71 of the female connector section 7B. Further, the top face 511 is located substantially flush with an end face of the female connector section 7A.

The head part 50 includes a tapered part 56 having an outside diameter in the vicinity of the top face 511 that gradually increases (in the axial direction) toward the barrel part 55, and a constant outside diameter part 57 provided at the distal end of the tapered part 56.

In addition, the tapered part 56 is formed with cutout portions 561 therein where the tapered part 56 is partly removed. Specifically, the head part 50 is formed with such cutout portions 561, where material is removed in areas ranging from the tapered part 56 to the constant outside diameter part 57.

This ensures that when the male connector section 6 of the connector 5A', which is connected to (inserted into) the connector 5A, is pulled off, i.e., when the connected condition (locked condition) is released, the valve element 51 (the head part 50) can enter easily into the first cavity 731 of the cap section 73, and therefore, the slit 512 can be closed more reliably.

In addition, the head part 50 is provided with two protuberant contact portions 52, which are pressed at times when the slit 512 is closed. The two contact portions 52 are formed in the vicinity of the top face 511 of the head part 50, and project in directions opposite to the directions (the directions of the arrows in FIG. 6) in which the slit 512 is closed.

The presence of the contact portions 52 ensures that when the head part 50 is inserted into the first cavity 731 of the cap section 73, the inner peripheral surface 734 of the first cavity 731 presses against the contact portions 52, so that the slit 512 can be closed more reliably (see FIG. 7). In addition, this makes it possible to enhance pressure resistance against the pressure of the liquid inside the connector 5A (internal pressure).

When the connector 5A' is not connected to the male connector section 6, the head part 50, configured as described above, is inserted into the first cavity 731 of the cap section 73, with the slit 512 being closed (see FIG. 7).

As shown in FIG. 6, the barrel part 55 includes a bellows-like cylindrical body. Specifically, the barrel part 55 has a bellows-like overall shape, in which large diameter ring portions 552 and small diameter ring portions 553 are alternately arrayed along the axial direction. Such a barrel part 55 functions as a deforming section (urging means), for urging the valve element 51 from the distal side toward the proximal side (i.e., in the direction in which the head part 50 is inserted into the first cavity 731).

Since the barrel part 55 functions as a deforming section, it is unnecessary to separately provide a component part on the connector 5A serving as an urging means. Therefore, a reduction in the number of component parts, and simplification in structure, can be realized.

In addition, although the barrel part 55 provides most of the restoring force for restoring the valve element 51 from the distal side toward the proximal side, the head part 50 may also provide a portion of the restoring force.

As shown in FIGS. 1 and 2, the connector 5A is provided with the lock mechanisms 10A to 10C, which are arranged in a dispersed manner. Specifically, in the connector 5A, the lock mechanism 10A is arranged in the vicinity of the female connector section 7B on the z-axis negative side (adjacent to the z-axis negative side) thereof. The lock mechanism 10B is arranged in the vicinity of the male connector section 6 on the z-axis negative side thereof. The lock mechanism 10C is arranged in the vicinity the female connector section 7A on the z-axis negative side thereof. The lock mechanisms 10A to 10C have substantially identical configurations; taking this into account, therefore, the lock mechanism 10A will be described as representative.

The lock mechanism 10A includes a male lock section 8A and a female lock section 9A. The male lock section 8A and the female lock section 9A operate to maintain a connected condition, in a condition where the connector 5A (the female connector section 7B) and the connector 5A' (the male connector section 6) are connected to each other.

As shown in FIGS. 3 to 5, the male lock section 8A as a whole is formed so as to project in parallel to the direction of connection between the connectors 5A and 5A' (the x-axis direction). The male lock section 8A includes a base part (male lock section main body) 81, a projected part 82 that projects from the base part 81, a pair of claw parts 83A, 83A provided on the projected part 82, and urging parts 84, which act to urge each of the claw parts 83A, respectively.

The base part 81 has an elongate (rectangular parallelepiped) shape. In the x-axis negative direction relative to the base part 81, a projected part 82 is formed that projects in the x-axis negative direction.

In z-axis directions (the upper and lower directions in FIG. 1) relative to the projected part 82, the elongate claw parts 83A and 83A are provided respectively. Both of the claw parts 83A, 83A have end portions 831, which are capable of moving toward and away from each other along the z-axis direction (see also FIGS. 1 and 2).

A first male-side engaging part 832, formed as if the end portion 831 were partially cut out (lost), is provided on an end portion 831 of each of the claw parts 83A.

In addition, in both side surfaces of each claw part 83A, a second male-side engaging part 833 is provided in a recessed shape (see FIG. 5).

The urging part 84 is provided on the x-axis negative side, between the projected part 82 and the claw part 83A. Each urging part 84 urges each claw part 83A, respectively, so that respective end portions 831 (the first male-side engaging parts 832) of both the claw parts 83A, 83A separate away from each other.

The female lock section 9A is disposed on the y-axis negative side of the male lock section 8A, adjacent thereto. In addition, substantially similar to the male lock section 8A, the female lock section 9A as a whole is formed parallel to the direction of connection between the connectors 5A, 5A' (i.e., in the x-axis direction).

The female lock section 9A has a substantially tubular overall shape.

As shown in FIGS. 3 to 5, the female lock section 9A is provided with a first female-side engaging part (engaging part) 91, which is capable of engagement with each of the first male-side engaging parts 832 of the male lock section 8A of the connector 5A', second female-side engaging parts 92, which are capable of engagement with each of the second male-side engaging parts 833 of the male lock section 8A of the connector 5A', and operating parts 93 that are capable of operating each of the claw parts 83A of the male lock section 8A of the connector 5A'.

As shown in FIG. 3 (also in FIG. 4), the first female-side engaging part 91 is formed such that an inner peripheral portion (inside diameter) of the female lock section 9A on the opening part 94 side thereof gradually diminishes along the x-axis positive direction (the leftward direction in FIG. 4). As shown in FIG. 3(c), when an end portion 911 of the first female-side engaging part 91 engages with the first male-side engaging parts 832 of the male lock section 8A of the connector 5A', the connector 5A (the female lock section 9A) and the connector 5A' (the male lock section 8A) are placed in a locked condition. Herein, the term "locked condition" implies a condition in which the connector 5A (the female lock section 9A) and the connector 5A' (the male lock section 8A) are fully connected with each other, and more specifically, a condition in which the connection between the connector 5A and the connector 5A' is not released, unless the operating parts 93 of the female lock section 9A of the connector 5A, to be described later, are operated.

As shown in FIG. 5, the second female-side engaging parts 92 are each provided so as to project from an intermediate location on the inner peripheral portion of the female lock section 9A. As shown in FIG. 5(b), when the second female-side engaging parts 92 engage with the second male-side engaging parts 833 of the male lock section 8A of the connector 5A', the connector 5A and the connector 5A' are placed in a half-locked condition. Herein, the term "half-locked condition" implies a condition in which the connector 5A and the connector 5A' are not fully connected with each other, and more specifically, a condition in which the connector 5A and the connector 5A' can be easily moved away from each other.

As shown in FIG. 4, the operating parts 93 include small pieces, which are provided in the x-axis positive direction relative to the first female-side engaging part 91. The operating parts 93 each operate (press) the claw parts 83A respectively, so that end portions 831 of both of the claw parts 83A of the connector 5A' (the male lock section 8A) are brought toward each other in the locked condition.

The male lock section 8A and the female lock section 9A, configured as described above, make up portions that can be coupled respectively to the female lock section 9A and the male lock section 8A of the connector 5A'.

Further, in the connector 5A, the lock mechanisms 10A-10C have the same configuration. Therefore, when the lock mechanisms 10A to 10C are designed, the configurations of the other lock mechanisms also are determined by determining the configuration of one of the lock mechanisms. This facilitates designing of the connector 5A. Also, the configuration of the connector 5A is comparatively simple, and therefore, the connector 5A is easily manufactured.

In addition, since the same lock mechanism can be used, the same product (i.e., the connector 5A) can be manufactured, so that the product itself can be manufactured inexpensively.

Next, the process of connecting (in a half-locked condition, a locked condition, and an unlocked condition) the connector 5A and the connector 5A' will be described below. In the connection process, the female lock section 9A of the lock mechanism 10A of the connector 5A and the male lock section 8A of the lock mechanism 10B of the connector 5A' are connected together, while simultaneously, the male lock section 8A of the lock mechanism 10A of the connector 5A and the female lock section 9A of the lock mechanism 10B of the connector 5A' are connected together. The connection process between the female lock section 9A of the lock mechanism 10A of the connector 5A and the male lock section 8A of the lock mechanism 10B of the connector 5A' is the same as the connection process between the male lock section 8A of the lock mechanism 10A of the connector 5A and the female lock section 9A of the lock mechanism 10B of the connector 5A'. Taking this into account, therefore, the connection process for the former combination will be described below as representative.

As shown in FIG. 1 (also in FIGS. 3(a) and 5(a)), starting from the condition where the connector 5A and the connector 5A' are separated from each other, the male lock section 8A of the connector 5A' is brought closer in proximity to the female lock section 9A of the connector 5A.

As shown in FIG. 3(a), as the male lock section 8A of the connector 5A' is inserted into the female lock section 9A of the connector 5A, the first female-side engaging part 91 of the connector 5A presses against the claw parts 83A of the connector 5A', in opposition to the urging forces of the urging parts 84 of the connector 5A'.

When the male lock section 8A of the connector 5A' is pressed further into the female lock section 9A of the connector 5A, as shown in FIG. 3(b), the second male-side engaging parts 833 of the connector 5A' engage with the second female-side engaging parts 92 of the connector 5A, as shown in FIG. 5(b), i.e., the connector 5A' and the connector 5A are placed in a half-locked condition. In this instance, the male lock section 8A (the opening part 623) of the connector 5A' and the female lock section 9A (the top face 511) of the connector 5A are placed in contact with (in proximity to) each other. This ensures that, when shifting from the half-locked condition into the locked condition, the end face of the male connector section 6 of the connector 5A' can quickly press against the top face 511 of the valve element 51 of the connector 5A.

When the male lock section 8A of the connector 5A' is pressed even further into the female lock section 9A of the connector 5A, engagement between the second male-side engaging parts 833 of the connector 5A' and the second female-side engaging parts 92 of the connector 5A is released, i.e., the half-locked condition is released.

From this condition, when the male lock section 8A of the connector 5A' and the female lock section 9A of the connector 5A are brought closer toward each other, the first male-side engaging parts 832 of the connector 5A' engage with the first female-side engaging part 91 of the connector 5A, i.e., the connector 5A' and the connector 5A are placed in a locked condition (see FIG. 3(c)). Consequently, shifting from the half-locked condition to the locked condition can easily be achieved.

As shown in FIG. 8, in the locked condition (connected condition), the opening part 623 of the male connector section 6 of the connector 5A' presses in the axial direction against the top face 511 of the head part 50 of the connector 5A. As a result, the barrel part 55 becomes deformed (compressed) in the axial direction, and the head part 50 moves from the first cavity 731 into the second cavity 723. The head part 50, which has resided inside the first cavity 731 restricted by the inner peripheral surface 734 of the first cavity 731, now moves into the second cavity 723, such that the restriction on the outer peripheral surface of the head part 50 is released or moderated. Consequently, as a result of being compressed in the axial direction, the head part 50 can be enlarged sufficiently in diameter, in the directions of the arrows in FIG. 8, namely, the head part 50 can be deformed sufficiently. Therefore, the slit 512 can be opened assuredly and sufficiently. In addition, as a result, the liquid passage 621 in the male connector section 6 of the connector 5A', and the cavity (hollow portion) of the internal projection 725 of the female connector section 7B of the connector 5A, communicate with each other, i.e., are connected so as to permit liquid to flow therethrough via the valve element 51 (the slit 512). Accordingly, liquid can pass smoothly therethrough, for example, when an infusion, a transfusion, nutrient dosing, or the like, is carried out.

Further, in the locked condition, the opening part 623 of the male connector section 6 of the connector 5A' presses against the head part 50 of the valve element 51, in opposition to the urging force of the barrel part 55 of the valve element 51, so that the opening part 623 of the male connector section 6 and the top face 511 of the head part 50 (the valve element 51) are securely placed in contact with each other. Consequently, liquid-tightness at the connection between the male connector section 6 and the female connector section 7B can be maintained, i.e., such sections can securely be connected in a liquid-tight manner.

In addition, the locked condition of the connector 5A' and the connector 5A can be released by operating the operating parts 93 of the connector 5A.

In other words, starting from the locked condition shown in FIG. 4(a), the claw parts 83A of the connector 5A' are pressed by the operating parts 93 of the connector 5A, as shown in FIG. 4(b). As a result, engagement between the first female-side engaging part 91 of the connector 5A and the first male-side engaging parts 832 of the connector 5A' is released (disengaged).

Thereafter, as shown in FIG. 4(c), the connector 5A' is pulled, whereby the connector 5A' and the connector 5A separate away from each other.

Incidentally, it is preferable for the fitting force between the female connector section 7B of the connector 5A and the male connector section 6 of the connector 5A' to be comparatively small when engagement therebetween is released. This ensures that pressing forces exerted by the urging parts 84 of the connector 5A' and the urging force (elastic force) of the valve element 51 that presses the claw parts 83A against the inner peripheral surface of the first female-side engaging part 91 of the connector 5A can overcome the aforementioned fitting force, so that the connector 5A' becomes disengaged resiliently from the connector 5A. Thus, the connector 5A' can easily be released from the connector 5A.

The connection process is performed in the same manner also between the male lock section 8A of the lock mechanism 10A of the connector 5A and the female lock section 9A of the lock mechanism 10B of the connector 5A'.

In this manner, the connector 5A and the connector 5A' can be fully connected, i.e., can be placed in a locked condition by a simple operation, in which the lock mechanism 10A of the connector 5A' and the lock mechanism 10B of the connector 5A are pressed against each other.

In the locked condition, the female lock section 9A and the male lock section 8A of the connector 5A are connected respectively with the male lock section and the female lock section 9A of the connector 5A'. In other words, the locked condition as a whole is composed of the connection between the connectors 5A and 5A' at two different locations. This ensures that the connected condition between the connectors 5A and 5A' is firm, so that unintentional release of the connected condition can be prevented securely.

In addition, in order to release the locked condition, the operating parts 93 of the connector 5A and the operating parts 93 of the connector 5A must be pressed (operated) respectively. As a result, for example in a case where the connectors 5A and 5A' in the connected condition are grasped, even if the operating parts 93 on one side are pressed by mistake, whereby the male lock section 8A and the female lock section 9A on one side become unlocked, the operating parts 93 on the other side are not operated, and therefore, the locked condition of the male lock section 8A and the female lock section 9A on the other side is maintained. Accordingly, unintentional release of the connected condition can be prevented assuredly.

Further, simultaneously with attainment of the locked condition, the female connector section 7B of the connector 5A and the male connector section 6 of the connector 5A' are connected in a liquid-tight manner.

In addition, in the half-locked condition, deformation of the valve element 51 is restrained (prevented) from occurring. For example, in a case where an infusion tube set 1 is shipped, with the connector 5A and the connector 5A' set in the half-locked condition, the valve element 51 is prevented from remaining in a deformed state for a long period of time, until the infusion tube set 1 is put to use. Consequently, the valve element 51 can be prevented from becoming plastically deformed, with the result that the slit 512 becomes normally opened.

Moreover, in the connector 5A configured as shown in FIG. 1 (also in FIG. 2), the male lock section 8A and the female lock section 9A are arranged symmetrically about the center axis of the female connector section 7B. This is advantageous in that the male connector section 6 of the connector 5A' and the female connector section 7B of the connector 5A are easily connected in a straight-line fashion, whereby the top face 511 of the valve element 51 of the connector 5A and the opening part 623 of the male connector section 6 of the connector 5A' are brought into firm contact with each other, and liquid-tightness of the connection can be maintained easily.

In addition, in the configuration of FIG. 1, while the male lock section 8A and the female lock section 9A are provided in a one-sided manner on the z-axis negative side relative to the female connector section 7B, the invention is not limited to this configuration. The lock sections may be arranged oppositely (dispersedly arranged) in upward and downward directions in FIG. 1, with the female connector section 7B interposed therebetween.

Also, the material constituting the connector 5A (exclusive of the valve element 51) is not particularly limited. Examples of suitable materials that can be used include various resins, such as polyvinyl chloride, polyethylene, polypropylene, cyclic polyolefins, polystyrene, poly-(4-methylpentene-1), polycarbonate, acrylic resin, acrylonitrile-butadiene-styrene copolymer, polyesters including polyethylene terephthalate, polyethylene naphthalate, etc., butadiene-styrene copolymer, and polyamides (e.g., 6-nylon, 6,6-nylon, 6,10-nylon, 12-nylon).

As shown in FIG. 9, the infusion dosing section 2 has an indwelling needle or catheter (in this embodiment, an indwelling needle 21) to be left indwelling in a patient's blood vessel 110, and an infusion dosing section side connector 26, which is connected to a proximal portion of the indwelling needle or catheter (in this embodiment, the indwelling needle 21).

Concerning the material constituting the indwelling needle 21 (or catheter), depending on the indwelling site, a metallic needle such as a winged phleboclysis needle may be used. However, polymer materials, examples of which include thermoplastic resins, such as polyolefins, including polyethylene, polypropylene, etc., polyesters, and polyurethane, preferably are used.

The infusion dosing section side connector 26 includes a female connector section 7A, which is capable of connection to the male connector section of the connector 5A, which in turn is connected to the second infusion tube 4a, a lock mechanism 10A capable of connection to the lock mechanism 10B of the connector 5A, and a male connector section 263.

In addition, the axis of the male connector section 263 and the axis of the female connector section 7B substantially coincide with each other, whereas the axis of the female connector section 7A is substantially orthogonal to the axes thereof. In other words, the male connector section 263 and the female connector section 7B are oriented in opposite directions, whereas the female connector section 7A is oriented in a direction substantially orthogonal to the male connector section 263 and the female connector section 7B.

In the infusion dosing section side connector 26, a tube 24 that passes through a stop clamp 25 and which can be fixed in a stroke is connected to the male connector section 263 in a liquid-tight manner. A male connector section 23 is connected to the distal side of the tube 24. The male connector section 23 is not particularly limited, and may be any of a luer connector, a luer lock connector and the like, which can be connected to an outlet port 211 of the indwelling needle or catheter in a liquid-tight manner. Among these examples, a luer lock connector is preferred in particular.

The indwelling needle 21 includes the outlet port 211 disposed at a proximal portion thereof. The male connector section 23 attached to the infusion dosing section side connector 26 is connected to the outlet port 211 in a liquid-tight manner.

Next, the first infusion tube 4b and the second infusion tube 4a will be described below. Since the first infusion tube 4b and the second infusion tube 4a have the same configuration, the second infusion tube 4a will be described as representative.

The second infusion tube 4a has a tube 41 which is flexible (soft) and which constitutes an infusion passage, a connector (tube-side connector) 43 provided at an end portion on one side (distal portion) of the tube 41, and a piercing needle 451, which has a sharp needle tip, is provided on the other side (in this embodiment, at an end portion on the other side (proximal portion)) of the tube 41, and serves as a connecting part to be connected to the side of an infusion bag (infusion vessel) (containing section) 31 containing an infusion.

Examples of materials that can be used to constitute the tube 41 include flexible polyvinyl chloride, ethylene-vinyl acetate copolymer, polyethylene, polypropylene, and polybutadiene, as well as other materials containing such materials as principal constituents thereof.

In addition, slide type forceps (slide forceps) 46 and a drip cylinder 44 are provided respectively at intermediate positions of the tube 41, serving as a flow rate regulating means for regulating the flow rate of the infusion. The slide forceps 46 are not particularly limited, and conventionally known slide forceps can be used. Examples of forceps that are usable include the forceps described in Japanese Laid-Open Patent Publication No. 2004-49319, for example.

Further, the slide forceps 46 may be constituted by other types, such as a roller-type forceps, which can regulate the flow rate.

A predetermined infusion is contained in the infusion bag 31. When a stopper (rubber stopper) of the infusion bag 31 is penetrated (pierced) by the piercing needle 451, the infusion bag 31 and the second infusion tube 4a are connected to each other through the piercing needle 451, and as a result, the infusion can be supplied from the infusion bag 31 to the side of the second infusion tube 4a.

The drip cylinder 44 is disposed in the vicinity of the piercing needle 451. The drip cylinder 44 enables visual confirmation of the flow rate of the infusion.

In addition, a check valve 49 is disposed between the connector 43 and the drip cylinder 44. The check valve 49 is a one-way valve, permitting flow in only one direction, from the infusion bag 31 toward the connector 5A. The check valve 49 may be disposed at any location between the connector 43 and the drip cylinder 44. Preferably, however, the check valve 49 is disposed nearer to the connector 43, and more preferably, inside of the connector 43.

The check valve 49 has a valve main body formed with a pair of plate-like opening/closing members (not shown) inside thereof, wherein the opening/closing members are in firm contact with each other due to the elasticity (restoring forces) thereof, so that the passage in the check valve 49 is kept closed. In the case that the infusion flows in a direction from the distal side toward the proximal side, a pressure due to the infusion is exerted on outside surfaces of the opening/closing members, thereby placing the opening/closing members in firm contact with each other. Therefore, the infusion does not flow from the distal side toward the proximal side.

On the other hand, in the case that the infusion flow is directed from the proximal side toward the distal side, a predetermined pressure due to the infusion is exerted on the proximal side (tapered surface) of each of the opening/closing members, and the opening/closing members are displaced away from each other by the pressure, so that the passage in the check valve 49 opens. Consequently, the infusion flows from the proximal side toward the distal side.

While the check valve 49 may be omitted in some cases, e.g., where an assured injection is promised by an infusion pump or the like, it is preferable for the check valve 49 to be installed. According to the second infusion tube 4a, even if an infusion is administered by exerting a certain degree of pressure from the first infusion tube 4b connected to the connector 5A of the second infusion tube 4a, the check valve 49 prevents the infusion from flowing toward and into the upstream side (proximal side) of the second infusion tube 4a. Thus, the patient can be dosed with the infusion(s) in a reliable manner.

The connector 43 is disposed at a distal portion of the tube 41. The connector 43 has a female connector section (not shown), which can be connected to the male connector section 6 of the connector 5A, and a lock mechanism (not shown), which can be connected to the lock mechanism 10C of the connector 5A. Such a configuration enables the connection between the connector 43 and the connector 5A. Further, in relation to the connection between the connectors 43 and 5A, the above-mentioned half-locked condition and locked condition can also be realized.

For example, until the second infusion tube 4a is placed in use, the male connector section 6 of the connector 43 is loosely fitted in such a position so as not to open the valve element 51 disposed in the female connector section 7B of the connector 5A. Specifically, until the second infusion tube 4a is to be used, the connector 43 is connected to the connector 5A in a half-locked condition. This ensures that the valve element 51 is kept in a non-deformed condition until a point in time immediately before the valve element 51 permits the infusion to flow therethrough. Thus, the valve element 5 can be used without spoiling or diminishing the functionality thereof.

Further, in the locked condition (connected condition), the male connector section 6 of the connector 43 and the female connector section 7B of the connector 5A are connected together in a liquid-tight manner, so that liquid can securely flow from the second infusion tube 4a into the connector 5A.

Now, operation (a method of use) of the infusion tube set 1 shall be described below.

A description will be made of the case where the second infusion tube 4a is used as a first infusion line (first infusion route) for dosing a patient with an infusion, and more specifically, as an infusion tube through which a basic liquid or the like principally flows, while the first infusion tube 4b is used as a second infusion line (second infusion route) for dosing the patient with an infusion, and more specifically, as an auxiliary route or an infusion tube through which, for example, a lipid emulsion, a therapeutic drug, an antibiotic agent or the like principally flows.

When the second infusion tube 4a is connected, first, for example, a maintenance medication is prepared in the infusion bag 31.

Next, the connector 43 is pushed into the connector 5A in order to connect them to each other.

Subsequently, as shown in FIG. 9, a stopper (rubber stopper) of the infusion bag 31 containing the infusion (medication) is penetrated (pierced) by the piercing needle 451 of the second infusion tube 4a. Owing thereto, the infusion bag 31 and the second infusion tube 4a are connected to each other via the piercing needle 451, resulting in a condition in which the infusion can be supplied from the infusion bag 31 to the side of the second infusion tube 4a.

Next, the passage in the second infusion tube 4a is primed.

Subsequently, the male connector section 6 of the connector 5A of the second infusion tube 4a is inserted and fitted into the female connector section 7A of the infusion dosing section side connector 26, which is connected to the outlet port 211 of the indwelling needle 21 that has been set indwelling in a blood vessel 110 (e.g., a peripheral vein or the like) of a patient. As a result, the female connector section 7A of the infusion dosing section side connector 26 and the male connector section 6 of the connector 5A of the second infusion tube 4a are connected to each other in a liquid-tight manner. In this instance, the lock mechanism 10A of the infusion dosing section side connector 26 and the lock mechanism 10B of the connector 5A are placed in the locked condition, whereby easy disconnection thereof is prevented from occurring.

Next, by operating the slide forceps 46 of the second infusion tube 4a, the flow rate (dosing rate) of the infusion through the second infusion tube 4a is adjusted to a prescribed flow rate (prescribed dosing rate) for the maintenance medication, and dosing with the infusion is carried out in this condition.

Incidentally, the infusion dosing section side connector 26 may be omitted, such that the male connector section 6 of the connector 5A of the second infusion tube 4a is connected to the outlet port 211 of the indwelling needle 21.

Subsequently, when the first infusion tube 4b, which is used for administering, for example, an antibiotic agent at a predetermined time interval depending on the patient's condition, is connected, initially, physiological saline with the antibody agent dissolved therein is prepared in an infusion bag 32.

Next, the connector 43 of the first infusion tube 4b is pushed into the connector 5A' in order to connect them to each other.

Subsequently, a stopper (rubber stopper) of the infusion bag 32 containing the infusion is penetrated (pierced) by the piercing needle 451 of the first infusion tube 4b. Owing thereto, the infusion bag 32 and the first infusion tube 4b are connected to each other via the piercing needle 451, resulting in a condition in which the infusion can be supplied from the infusion bag 32 to the side of the first infusion tube 4b.

Next, the passage in the first infusion tube 4b is primed.

Subsequently, as shown in FIG. 10, the connector 5A' of the first infusion tube 4b is inserted into and connected to the connector 5A of the second infusion tube 4a. As a result, the female connector section 7B of the connector 5A of the second infusion tube 4a and the male connector section 6 of the connector 5A of the first infusion tube 4b are connected to each other in a liquid-tight manner. In this instance, the lock mechanism 10A of the second infusion tube 4a and the lock mechanism 10B of the first infusion tube 4b are placed in the locked condition, whereby easy disconnection thereof is prevented.

Next, by operating the slide forceps 46 of the first infusion tube 4b, the flow rate (dosing rate) of the infusion in the first infusion tube 4b is adjusted to a prescribed flow rate (prescribed dosing rate) for an antibiotic agent, and infusion is carried out in this condition.

In this manner, the patient can be dosed, respectively, with the maintenance medication from the second infusion tube 4a, and with the physiological saline containing the antibiotic agent dissolved therein from the first infusion tube 4b (i.e., the patient can be dosed with a mixture of liquids).

Further, in the case that additional infusion lines (infusion routes) are established, a connector 5A of another infusion tube (not shown) is connected to the connector 5A of the first infusion tube 4b, in the same manner as described above.

From then on, any number of infusion lines can be added in the same manner.

Incidentally, the method of using the infusion tube set 1, as mentioned above, is merely one example. However, the method is not limited to this example. For example, in a case where the patient is dosed with an infusion from the second infusion tube 4a, the infusion may be supplemented by use of the first infusion tube 4b.

In addition, the number of the infusion tube(s) in the infusion tube set according to the present invention may be one, or may be three or more.

Further, in the case that the infusion tube set includes a plurality of infusion tubes, in the present invention, the infusion tubes may all be the same, or the infusion tubes may all be different from each other, or only a portion of the infusion tubes may be the same.

Second Embodiment

Figure 11:
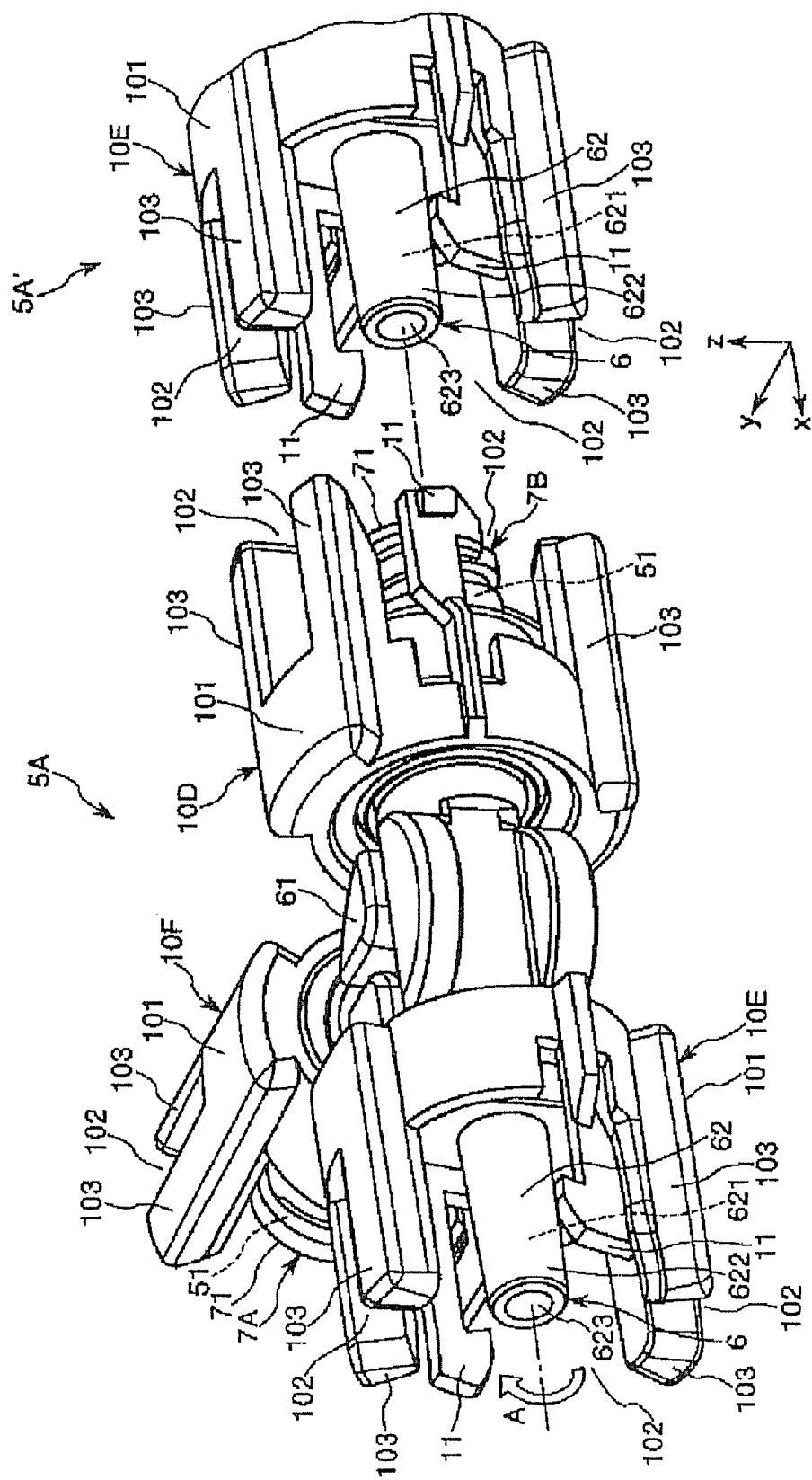
FIG. 11 is a perspective view showing a second embodiment of the connector according to the present invention.

FIG. 11 is a perspective view showing a second embodiment of the connector according to the present invention.

Referring to this figure, the second embodiment of the connector and the infusion tube set according to the present invention will be described below. The following description will be centered on the differences from the above-described embodiment, and descriptions of the same items already described above will be omitted.

The present embodiment is the same as the above-described first embodiment, except for certain differences in the configuration of the lock mechanism.

In a connector 5A (and in a connector 5A' as well), as shown in FIG. 11, a lock mechanism 10D is arranged on an outer peripheral part of a female connector section 7B, another lock mechanism 10E is arranged on an outer peripheral part of a male connector section 6, and another lock mechanism 10F is arranged on an outer peripheral part of a female connector section 7A. Since the lock mechanisms 10D to 10E are substantially the same in configuration, only the lock mechanism 10D will be described as representative.

The lock mechanism 10D includes a cylindrical section, which is disposed concentrically with the female connector section 7B, and which has a substantially cylindrical overall shape. A wall part 101 of the cylindrical section is formed with four deficit portions 102 therein. Each of the deficit portions 102 defines a portion where the wall part 101 is removed in an elongate area along the center axis direction of the cylindrical section (the female connector section 7B).

The deficit portions 102 respectively constitute female lock sections (function as female lock sections). In addition, those portions of the wall part 101 that are located between adjacent ones of the deficit portions 102, namely, four projected portions of the wall part 101 excluding the deficit portions 102 (hereinafter referred to as "projected portions 103") constitute male lock sections (function as male lock sections).

Thus, in the lock mechanism 10D, the four male lock sections (the projected portions 103) and the four female lock sections (the deficit portions 102) are alternately arranged along the outer circumferential direction of the female connector section 7B.

In the connector 5A, which is configured in this manner, when the connector 5A is connected with the connector 5A', the projected portions 103 of the connector 5A (the lock mechanism 10D) are fitted into the corresponding deficit portions 102 of the connector 5A' (the lock mechanism 10E). Simultaneously, the corresponding projected portions 103 of the connector 5A' (the lock mechanism 10E) are fitted into the deficit portions 102 of the connector 5A.

In the locked condition, therefore, connection of the connector as a whole is effected by connection between the connectors 5A and 5A' at the four different locations. This results in the connected condition of the connectors 5A and 5A' being enhanced in rigidity, so that unintentional release of the connected condition can be prevented more securely.

In addition, the connectors 5A and 5A' each may have an auxiliary means for assisting in maintenance of the locked condition. The auxiliary means is not particularly limited. For example, the auxiliary means may include engaging pieces 11, which are capable of mutual engagement in the locked condition, as shown in the figure. Each of the engaging pieces 11 projects toward the x-axis negative direction inside of the lock mechanism 10D.

The engaging pieces 11 of the connector 5A are configured such that when they are in engagement with the engaging pieces 11 of the connector 5A' in the locked condition, the pieces can be disengaged by pressing the engaging pieces 11 inwardly.

In addition, as mentioned above, the lock mechanism 10D is substantially cylindrical in overall shape. This ensures that the lock mechanism 10D can be used, or be connected to the lock mechanism 10E of the connector 5A', at any of a plurality of rotational angles about the center axis of the female connector section 7B, by rotating the lock mechanism 10D about the center axis thereof (i.e., in the direction of the arrow A in FIG. 11).

For example, in a case where the tube 24 in FIG. 9 has been twisted, twisting of the tube 24 can be eliminated through use of the connector 5A, after rotating the connector 5A in a direction reverse to the direction of twisting.

In addition, even when the connector 5A is rotated while in use, the connection conditions, such as the fixing force (connecting force) of the lock mechanism 10A, are not changed. In other words, in such a case, unintentional release of the connected condition can securely be prevented from occurring.

While the connector and the infusion tube set according to the present invention have been described with reference to the embodiments shown in the drawings, the invention is not limited to such embodiments. The components of the connector and the infusion tube set may be replaced by other arbitrary configurations, which can exhibit functions the same or equivalent to those mentioned above. Additionally, arbitrary components or structures may be added to the aforementioned embodiments.

In addition, the connector and the infusion tube set according to the present invention may comprise an arbitrary combination of two or more configurations (features) of the above-described embodiments.

For example, the lock mechanisms in the second embodiment may be configured such that the lock mechanisms can be placed in a half-locked condition, similar to the lock mechanisms of the first embodiment.

INDUSTRIAL APPLICABILITY

The connector according to the present invention includes a male connector section having a male-side cavity, a female connector section having a female-side cavity to which an other male connector section the same as the male connector section can be connected, a seal member formed from an elastic material for maintaining liquid tightness between the connector sections when the other male connector section and the female connector section are connected to each other, and lock mechanisms disposed respectively on the male connector section side and the female connector section side for maintaining the connected condition of the connector sections when the other male connector section and the female connector section are connected to each other. Each of the lock mechanisms has a male lock section formed to project in parallel with the direction of connection between the connector sections, and a female lock section disposed adjacent to the male lock section and which is parallel to the direction of connection, and to which another male lock section the same as the male lock section can be coupled. Therefore, in the connected condition in which the connectors are connected with each other, the female lock section and the male lock section on the side of the connector section on one side, and the female lock section and the male lock section on the side of the connector section on the other side, are connected together respectively. In other words, in the connector as a whole, the connected condition is composed of connections at two different locations. As a result, the connected condition is made rigid, and unintentional release of the connected condition can securely be prevented from occurring. Further, even if one of the connections at the two locations is released, the other connection is maintained. This ensures that unintentional release of the connected condition can reliably be prevented from occurring. Accordingly, the connector of the present invention has industrial applicability.

The invention claimed is:

1. A connector including:
a male connector section having a male-side cavity;
a female connector section having a female-side cavity to which another male connector section the same as the male connector section can be connected;
a seal member formed from an elastic material for maintaining liquid tightness between the connector sections when the other male connector section and the female connector section are connected to each other; and
a first lock mechanisms disposed on the male connector section side, wherein when the male connector section and another female connector section the same as the female connector section are connected to each other, the first lock mechanism maintains a connected condition of the connector sections;
a second lock mechanism disposed on the female connector section side, wherein when the female connector section and the other male connector section are connected to each other, the second lock mechanism maintains a connected condition of the connector sections;
wherein the first lock mechanism has a first male lock section formed to project in parallel to the direction of connection between the connector sections, and a first female lock section, which is formed adjacent to the first male lock section and parallel to the direction of connection, and which is capable of being connected to another male lock section having the same configuration as the first male lock section, and
wherein the second lock mechanism has a second male lock section formed to project in parallel to the direction of connection between the connector sections, and a second female lock section, which is formed adjacent to the second male lock section and parallel to the direction of connection, and which is capable of being connected to another male lock section having the same configuration as the second male lock section.

2. The connector according to claim 1, wherein in the connected condition, the male-side cavity of the other male connector section and the female-side cavity of the female connector section communicate with each other so as to permit a liquid to flow therethrough.

3. The connector according to claim 1, wherein each of the male connector section and the female connector section is tubular in shape, and the male lock section and the female lock section are disposed symmetrically about a center axis of the connector section.

4. The connector according to claim 1,
wherein the male lock section has a pair of long claw parts capable of moving toward and away from each other, and an urging part provided on one end side of both of the claw parts and operative to urge the claw parts, so as to move the claw parts away from each other on the other end side; and
the female lock section has engaging parts capable of engagement respectively with the claw parts of the other male lock section, which are the same as the claw parts of the male lock section, and an operating part operable to cause both the claw parts of the other male lock section, which are the same as the claw parts of the male lock section, to move toward each other.

5. The connector according to claim 1, wherein the seal member is fixed to the female-side cavity of the female connector section, and has a surface, which is placed in secure contact with an end part of the other male connector section in the locked condition, and a slit formed in the surface, which is opened in the locked condition.

6. The connector according to claim 1, including a plurality of the female connector sections,
wherein at least one of the female connector sections and the male connector section are disposed so that center lines thereof are substantially orthogonal to each other.

7. The connector according to claim 1, including a plurality of the female connector sections,
wherein at least one of the female connector sections and the male connector section are disposed so that center lines thereof are parallel to each other, and an opening part of the female connector section and an opening part of the male connector section are oriented in opposite directions.

8. An infusion tube set including:
the connector as set forth in claim 1; and
a tube assembly having a tube, and a tube-side connector, which is disposed at one end part of the tube, and which can be connected to the connector.

9. A connector including:
a male connector section having a male-side cavity;
a female connector section having a female-side cavity to which another male connector section the same as the male connector section can be connected;
a seal member formed from an elastic material for maintaining liquid tightness between the connector sections when the other male connector section and the female connector section are connected to each other; and lock mechanisms disposed respectively on the male connector section side and the female connector section side for maintaining the connected condition of the connector sections when the other male connector section and the female connector section are connected to each other;

wherein each of the lock mechanisms has a male lock section formed to project in parallel to the direction of connection between the connector sections, and a female lock section, which is formed adjacent to the male lock section and parallel to the direction of connection, and to which another male lock section the same as the male lock section can be coupled, wherein each of the male connector section and the female connector section is tubular in shape, and pluralities of the male lock sections and the female lock sections are alternately arranged along an outer circumferential direction of the connector section, the lock mechanisms are disposed respectively on an outer peripheral part of the connector section, and are substantially cylindrical in overall shape, and the cylindrical wall part is provided with a plurality of deficit portions, where material is made deficient in long-shape areas along the center axis direction, the female lock sections being constituted by the deficit portions, and the male lock sections being constituted by portions of the wall part that are located between adjacent ones of the deficit portions.

10. The connector according to claim 9, wherein in the connected condition, the male-side cavity of the other male connector section and the female-side cavity of the female connector section communicate with each other so as to permit a liquid to flow therethrough.

11. The connector according to claim 9, wherein each of the male connector section and the female connector section is tubular in shape, and the male lock section and the female lock section are disposed symmetrically about a center axis of the connector section.

12. The connector according to claim 9, wherein each of the lock mechanisms can be used at any of a plurality of rotational angles about the center axis of the connector section.

13. The connector according to claim 9, wherein the seal member is fixed to the female-side cavity of the female connector section, and has a surface, which is placed in secure contact with an end part of the other male connector section in the locked condition, and a slit formed in the surface, which is opened in the locked condition.

14. The connector according to claim 9, including a plurality of the female connector sections,
wherein at least one of the female connector sections and the male connector section are disposed so that center lines thereof are substantially orthogonal to each other.

15. The connector according to claim 9, including a plurality of the female connector sections,
wherein at least one of the female connector sections and the male connector section are disposed so that center lines thereof are parallel to each other, and an opening part of the female connector section and an opening part of the male connector section are oriented in opposite directions.

16. An infusion tube set including,
the connector as set forth in claim 9; and
a tube assembly having a tube, and a tube-side connector, which is disposed at one end part of the tube, and which can be connected to the connector.

* * * * *